United States Patent

Kovács et al.

[11] Patent Number: 5,583,105
[45] Date of Patent: Dec. 10, 1996

[54] ORAL PHARMACEUTICAL PREPARATION

[75] Inventors: István Kovács; Márta Jusztin; Erzsébet Takács; Zoltan Balázs, all of Debrecen; Ildikó Kiss, Ebes; Zsolt Varga, Debrecen; Sándor Jancsó, Debrecen; Csaba Heim, Debrecen; IldikóKánya née Korcsmáros, Debrecen; Erzébet Erdöháti, Konyá; Márta Jarabin, Debrecen, all of Hungary

[73] Assignee: Biogal Gyogyszerguar Rt, Debrecen, Hungary

[21] Appl. No.: 414,496

[22] Filed: Mar. 31, 1995

[30] Foreign Application Priority Data

Nov. 21, 1994 [DE] Germany ............... 94 03 328

[51] Int. Cl.⁶ .................. A61K 9/113; A61K 9/66; A61K 38/13; A61K 47/14
[52] U.S. Cl. .................. 514/11; 424/452; 424/455; 514/785; 514/885; 514/937; 514/938
[58] Field of Search .................. 514/11, 785, 885, 514/937, 938; 424/452, 455

[56] References Cited

U.S. PATENT DOCUMENTS

| | | | |
|---|---|---|---|
| 4,388,307 | 6/1983 | Cavanak | 424/177 |
| 4,861,580 | 8/1989 | Janoff et al. | 424/4.1 |
| 5,154,930 | 10/1992 | Popescu et al. | 424/489 |
| 5,234,695 | 8/1993 | Hobbs et al. | 424/489 |
| 5,342,625 | 8/1994 | Hauer et al. | 424/455 |
| 5,364,632 | 11/1994 | Benita et al. | 424/450 |
| 5,447,729 | 9/1995 | Belendvik et la. | 424/490 |

FOREIGN PATENT DOCUMENTS

| | | |
|---|---|---|
| 0387647 | 9/1990 | European Pat. Off. . |
| 0391369 | 10/1990 | European Pat. Off. . |
| 0570829 | 11/1993 | European Pat. Off. . |
| 0589843 | 3/1994 | European Pat. Off. . |
| 0295765 | 11/1991 | Germany . |
| 298351 | 2/1992 | Germany . |
| 2270842 | 3/1994 | United Kingdom . |
| 9209299 | 6/1992 | WIPO . |
| 9318852 | 9/1993 | WIPO . |
| 9320833 | 10/1993 | WIPO . |
| 9408603 | 4/1994 | WIPO . |
| 9408605 | 4/1994 | WIPO . |

*Primary Examiner*—Shep K. Rose
*Attorney, Agent, or Firm*—Keil & Weinkauf

[57] ABSTRACT

The invention relates to an oral multiple emulsion pre concentrate comprising a surface active agent, ethanol a lipophilic and/or an amphiphilic solvent. The composition comprising from about 5 to about 30% by weight of cyclosporin, from about 5 to about 30% by weigh of tocopheryl polyethylene glycol carboxylic acid ester, from about 5 to about 20% by weight of ethanol, from about 20 to about 55% by weight of a lipophylic solvent and/or from about 10 to about 55% by weight of an amphiphilic solvent, and if desired from about 10 to about 20% by weight of co-tenside.

14 Claims, 1 Drawing Sheet

ORAL PHARMACEUTICAL PREPARATION

The invention relates to a multiple emulsion pre-concentrate comprising a surface active agent, ethanol and a lipophilic and/or an amphiphilic solvent. The cyclic poly-N-methylated undecapeptides, belonging to the family of cyclosporins, commonly possess immunosuppressive, anti-inflammatory, anti-fungal and anti-parasitic activity. Since the discovery of the cyclosporin A, which is the first isolated representative of them, a wide variety of naturally occurring cyclosporins have been isolated and identified, many of them have been prepared by semisynthesis or total-synthesis.

The primary indication of cyclosporin A is the prevention of rejection of organ transplants. Further area of immuno-suppressive therapy is the treatment of serious chronic autoimmune diseases (lupus erythematosus, glomerulonephritis, haemolytic anemia, myasthenia gravis, multiple sclerosis). In case of organ/tissue transplantation the treatment of the patients starts with the intravenous administration of the suitable preparation, and later during the therapy oral pharmaceutical forms are used. Concerning the latter preparations it is difficult to develop the optimum composition, since due to the chemical structure and low water-solubility of cyclosporin, its oral absorption is relatively poor. Therefore during the development of the oral pharmaceutical preparations containing cyclosporin, the most important aim is to create the composition of the product, resulting a significant improvement in the absorption of the active ingredient.

A number of method are known from the patent literature, where the active ingredient is dissolved in the mixture of natural vegetable oils or synthetic fatty acid esters and various surfactants such as transesterified polyethylene glycols, fatty acid saccharide esters, sorbitan-fatty acid esters, the solubility of which is optionally increased by adding ethanol (Swiss patent No. 636,013).

The forms of pharmaceutical compositions obtained in the above mentioned way and containing the dissolved cyclosporin have the following common feature: in the case of drink-solution the patient, before taking it, makes an "oil-in-water" (o/w) emulsion ex tempore, or in the case of soft gelatin capsule, after the disintegration in the gastric juice, an o/w emulsion is formed, and its oil phase keeps the active ingredient in dissolved form. Of course, the fact itself, that the active ingredient is dissolved in the oily phase is not enough for the absorption, the drug to become dissolved also in the gastrointestinal juice. This is ensured by the surface active materials applied, which fact is emphasized in the German patent application No. 3.930 928 claiming a process for the preparation of a microemulsion pre-concentrate.

This preparation contains a hydrophilic phase, and fatty acid triglycerides as lipophilic phase and a surface active material.

The microemulsion in colloidal size ensures great specific surface for the transfer into the body fluids.

The basic problem with the solution applied first of all in drink-solutions and in soft gelatin capsules described in different patents in addition to the limited absorption is the instability of the oil phase; the fatty oils become rancid and the unpleasant taste of medicine hampers its use. Further disadvantage can be the precipitation of the active ingredient or the excipient at lower temperature. This fact does not allow the storage of the composition in a cool place, which otherwise would be desirable from the point of view of the chemical stability itself. Moreover, the surface active materials representing the greater part of the solution are not compatible with the gelatin film and make the preparation of soft gelatin capsule more difficult.

The stability problems connected with the excipients and vehicles can be avoided by the process disclosed in the Hungarian patent specification No. 208 491, where the active ingredient is dissolved in ethanol/propylene glycol mixture containing poloxamer as surface active agent. Applying this solution as a drink-solution, a suspension is obtained the particle size of which is also near colloidal, and from this suspension the degree of absorption is almost the same as that of other commercially available compositions.

From the point of view of formulation an other problem arises, namely it is well known that the solutions prepared with hydrophilic solvent can not be filled into gelatin capsule, consequently for the preparation of both suspension and emulsion forming systems only lipophilic and/or amphiphilic media can be used.

A further criteria of the preparation of gelatin capsule is that both the excipients and the whole solution has to be compatible with the shell, not making it softer or fragile.

The oral compositions according to the patent specifications mentioned above, and containing the cyclosporins in solution, form emulsion in aqueous media, in special case microemulsion during the therapeutic application. Generally nonionic or in some cases anionic surface active ingredients being present in significant quantity in the pharmaceutical preparation, make possible the absorption of the active ingredient under psysiological conditions.

In disorders relating to the neurohumoral as well as the hepatic system and considering the side effect of the cyclosporins, too, (gastrointestinal and hepatic disturbances) the absorption of the active ingredient(s) from the gastrointestinal tract becomes problematic because of oligocholia. The presence of bile acids and their salts by all means is necessary for the degradation and digestion of carriers with fatty character and for the absorption of the active ingredients dissolved in them. Though the emulsion and microemulsion pre-concentrates developed for oral cyclosporin preparations (Sandimmun, Sandimmun Optoral, Sandimmun Neoral, producer: Sandoz AG; CH) improve the absorption of active ingredient, also in the case of decreased quantity of bile salts, however they do not contain any component which could substitute them (SCRIPT No. 1861. Oct. 5th 1993, p. 21, Aerzte Ztg. 5.10. 1993. p. 2/4.).

The object of the present invention is the preparation of a cyclosporin-containing, well absorbing oral composition the bioavailability of which is higher then 40–48%, i.e. the bioavailability of the above described composition.

Beside assuring the chemical stability of the cyclosporin, our aim was to develop such a composition, from which neither the active ingredient, nor the excipients precipitate during the storage in a cool place (5°–15° C.) which makes possible to prolong the shelf life of the preparation. However, our aim was to develop a composition in which the excipients are chemically stabile, they do not become oxidized and rancid, since they are selected properly and the oxidation is inhibited by a suitable excipient.

During the investigation of the excipients promoting the dissolution and absorption of the active ingredient into the gastrointestinal fluid, we have surprisingly found, that the absorption of tocopheryl polyethylene glycol polycarboxylic acid esters does not require the presence of bile acids, moreover the absorption of drugs, in our case the cyclosporin, solubilized by them is significantly improved as well. To our experiments we favoured the product of the Eastman Fine Chemicals (Kingsport, Tenn. 37662-5300, USA) being available under the trade name of Vitamin E TPGS. The Vitamin E TPGS is chemically d-α-tocopheryl polyethylene glycol 1000 succinate being stochiometrically defined, homogenous surfactant. Similarly to its building components, it is pharmaceutically acceptable, have no irritating and senzibilizing effect, it is not toxic (LD50>5 g/kg in white mouse).

During our research work a multiple emulsion pre-concentrates were prepared using Vitamin E TPGS and per se known vegetable and synthetic fatty oils as well as amphiphilic solvents. These solutions differ substantially e.g. from the liposomes described in international patent application No. WO 87/02219, which consist of vesicles formed by the tris-(hydroxymethyl)aminomethane salt of tocopheryl hemisuccinate and used first of all for parenteral and topical, seldom oral administration. The liposomes are prepared under special circumstances by ultra-sound treatment with large energy transfer.

Our aim was to prepare a cyclosporin solution with lipophilic and/or amphiphilic solvents, which can be easily applied in the form of drink-solution and/or gelatin capsule. When the solution according to the present invention containing the active ingredient is mixed with water, tea, fruit juice, or milk (cocoa) according the patients wish, a multiple emulsion (w/o/w type) forms spontaneously, without energy transfer. In the case of gelatin capsule the emulsion is formed in the gastric juice after the desintegration of the capsule.

From the point of view of formulation the solution having the composition: Cyclosporin A:Vitamin E TPGS:Miglyol 812: ethanol=10:30:50:10 seemed to be especially advantageous. Pouring 2–5 mls of this solution into. approximately 50 mls of water, a finely dispersed multiple emulsion is obtained with a particle size of (50–500 nm) near to the colloidal scale.

This high viscous solution can be filled at about 30° C. either into soft or hard gelatin capsule (LICAPS); also the latter is preferably hermetically sealed.

From the multiple emulsion having been formed or forming during the therapeutical application, the absorption of the active ingredients like cyclosporin is favourable. At the same time, beside the cyclosporin dose of 2.5–13 mg/kg die, the dose of Vitamin E being in this case identical, has to be taken into consideration too.

Recently in therapy more and more attention is paid to the Vitamin E because of its favourable physiological effect. In addition to the treatment of diseases connected with pregnancy as well as malabsorption and muscular dystrophy, it can advantageously be used as a free radical capturer for the prevention and therapy of heart and cardiovascular diseases, e.g. cardiac insufficiency (Stamfer M. J. et. al., New England J. of Med. 328 1444 (1993).

In our case the Vitamin E plays of special importance in the arachidonic acid metabolism; it influences the prostaglandine formation by inhibiting the arachidonic acid release and the enzyme activity of lipoxigenase, and by this way it inhibits the thrombocyta aggregation (Ellis, G. P., Progress in Medicinal Chemistry 25. Elsevier, Amsterdam, 1988). This effect of the Vitamin E can decrease the nephrotoxic effect of the cyclosporin, and from this point of view it is more favourable agent then the fish oil containing omega-3-unsaturated fatty acids (WO patent specification No. 87/06463), because its composition is determined and constant.

The daily dose of the orally administered Vitamin E can reach the 200–300 mg. Thus, it can not be considered to be toxic at all. In spite of this, especially because of the chronic administration required by the immunosuppressive therapy, the quantity of Vitamin E—in our case as adjuvant and excipient—has to be decreased.

Decreasing the ratio of this surfactant, the desired high dispersity grade of the emulsion is also reduced. Therefore, from the point of view of physico-chemical and pharmaceutical reasons it seemed practical to use complex emulgeator system.

The fact, that the tocopheryl polyethylene glycol succinic acid esters in the system we used are incompatible with the usually applied tensides of low HLB value, such as polyethylene glycol fatty acid esters and ethers caused difficulties for us. However we surprisingly found, that in suitable lipophilic and/or amphiphilic solvent or solvent mixtures applying sorbitan fatty acid esters characterized by low HLB values, such as sorbitan monolaurate, sorbitan monopalmitate, sorbitan monostearate and sorbitan monooleate (HLB values are 8.6, 6.7, 4.7, 4.3 respectively) as well as alkyl-polyglycol ether orthophosphoric acid esters (the product commercially available under the trade name Hostapat) a w/o/w type multiple emulsion can be obtained, where the size of the drops and thickness of the double layer in its inner phase does not exceed the 0.2–1.0 μm, whole of the w/o/w emulsion drop in the lipophilic solvent and lipophilic/amphiphilic cosolvent (described later) the 10 μm, and in amphiphilic solvent alone the 30 μm size.

Consequently the object of the present invention is an oral cyclosporin multiple emulsion pre-concentrate containing a surfactant, ethanol, a lypophilic and/or amphiphilic solvent in such a way, that the preparation comprises from about 5 to about 30% by weight of cyclosporin, from about 5 to about 30% by weight of tocopheryl polyethylene glycol carboxylic acid ester, from about 5 to about 20% by weight of ethanol, and from about 20 to about 55% by weight of a lipophilic solvent and/or from about 10 to about 55% by weight of an ampiphilic solvent and moreover if it is desired from about 10 to about 20% by weight of a cotenside.

The fatty oils applied are known from both the literature and the patent specifications mentioned above. In our case the solvents were used as vehicles and made possible to develop the object of the invention, that is the multiple emulsion pre-concentrate with the tensides and co-tensides. The Vitamin E TPGS is present not only as an emulsifying agent and adjuvant, but it inhibits the alteration of the above mentioned fatty oils preventing them to become rancid. Thus in our case it was not necessary to increase the number of the components of the composition with an antioxidant.

The disadvantage of the commercially available products is, that at lower temperature (5° to 15° C.) the surfactants solidify and occasionally the active ingredient precipitates from the solution. This fact does not allow to store the composition in a cool place, though the precipitated materials can be dissolved again by warming, it decreases the patient's confidence in the medicine. Therefore, the commercially available preparations has to be stored strictly at room temperature. This fact, however, significantly reduces the possibility of long-term storage.

Thus a stable solution, i.e. a multiple emulsion preconcentrate was developed, from which neither the active ingredient, nor the surfactant precipitate under the storage in a cool (5° to 15° C.) place. This was achieved by the suitable selection of the ratio of co-tensides and co-solvents.

The solution for drink-solution, i.e. the multiple emulsion pre-concentrate occasionally may contain 20% of ethanol to keep the solid or semisolid components in solution. Such an ethanol content causes no difficulties in case of a drink-solution, but in case of a capsule it reduces the stability of the shell and the high ethanol content requires a special hermetically sealed packaging of the capsule.

The high ethanol concentration was decreased by applying triethyl-citrate (Citroflex 2) or acetyl triethyl citrate (Citroflex 2A), which have a special advantage to compensate the softening effect of the filling material with the relative high tensid-content, and moreover it is suitable for the preparation of stabile, shape-keeping capsule with the required hardness.

The above described two co-solvents, i.e. the ethanol and triethyl citrate have a particular advantage, that in a w/o/w type multiple emulsion system they increase the dissolution of the active ingredient into the aqueous phase, namely, at the place of application into the gastro-intestinal fluid, and as a result, its absorption.

Since in the w/o/w type multiple emulsion system the inner phase is also water or aqueous solution, the ethanol and occasionally the triethyl-citrate or its derivate diffuse into this inner phase from the oily and amphiphilic solvent double layer. This diffusion is promoted by the fact, that the ethanol is freely miscible with water, and the triethylcitrate forms anaqueous solution of 6.5%. Since the cyclosporin is very soluble in both co-solvents, its dissolution into them becomes easier; in the gastro-intestinal tract after splitting the fatty barrier, the active ingredient via diffusion from this more concentrated solution distributes well on the gastric and intestinal mucosa and becomes absorbed.

The effects of the compositions according to the invention were determined in comparative animal trials.

The test materials were the capsule prepared according to Example 3 and Example 5. As a reference material the commercially available Sandimmun capsule was selected containing 25 mg of cyclosporin A (producer: Sandoz AG; CH).

6 male New Zealand rabbits were used in the animal tests, their weight were in the range of 2.1–2.8 kg. The animals received standard rabbit food (LATI) and tap water ad libitum. The animals were kept separately at 20°±2° C.

No food was given to the rabbits from the afternoon of the day before the treatment (12 hours long fasting).

3 capsules of both preparations were administered to the animals, this corresponds to about 30 mg cyclosporin A/kg body weight dose. The treatment was carried out in a double blind examination, and there were 2 weeks interval between the treatments. For the measurements 0.5–1 cm$^3$ of blood was taken from the ear vein of the rabbits into ready-to-use blood sampling tubes containing EDTA as anticoagulant. The blood samples were taken before the treatment and then 0.5, 1, 2, 3, 4, 6, 8, and 24 hours after the treatment. The samples were kept at 4° C. till they were analyzed. The determination of cyclosporin concentrations was carried out by TDx method. The instrument and reagents supplied by the Abbott Laboratories (USA) were suitable for the determination of the level of the active ingredient from whole blood by fluorescent polarization immune method using monoclonal antibodies.

BRIEF DESCRIPTION OF THE DRAWINGS

The mean and individual blood level values of the animals are shown on graphs of FIG. 1 and FIG. 2, where the cyclosporin concentration values (μg/l) are plotted against time. From the data it can be seen, that the blood-level values of the composition according to Example 3 are much higher than of Sandimmun capsule, and in addition in the case of the previous composition the maximum blood-level is reached in a shorter time, already one hour after the administration. The AUC values (area under curve) for 0–24 hours period are 5.953 mg.h/l (±SE: 1.322) for the product according to the invention and 1.611 mg.h/l (iSE: 0.280) for the parallel tested Sandimmun capsule, showing the substantially better bioavailability of our composition. The blood level values of the composition prepared according to Example 5 (FIG. 2) are also significantly higher than that of the Sandimmun capsule. The AUC value for 0–24 hours period is 5.52 mg.h/l (±SE: 0.784) against the value of 2.978 mg.h/l (iSE: 0.509) for the Sandimmun capsule. A further important feature of the invention is, that the blood level value decreases more slowly, when the composition according to the present invention is applied, indicating that the effect of the composition lasts for longer period providing the possibility of maintaining a steady blood level during long lasting treatment.

The accelerated and storage stability test of the capsules prepared according to the invention were also carried out. The active ingredient content was determined by HPLC method, according to the Ph. Eur. 2nd. V.6.20.4.

Figure 1:
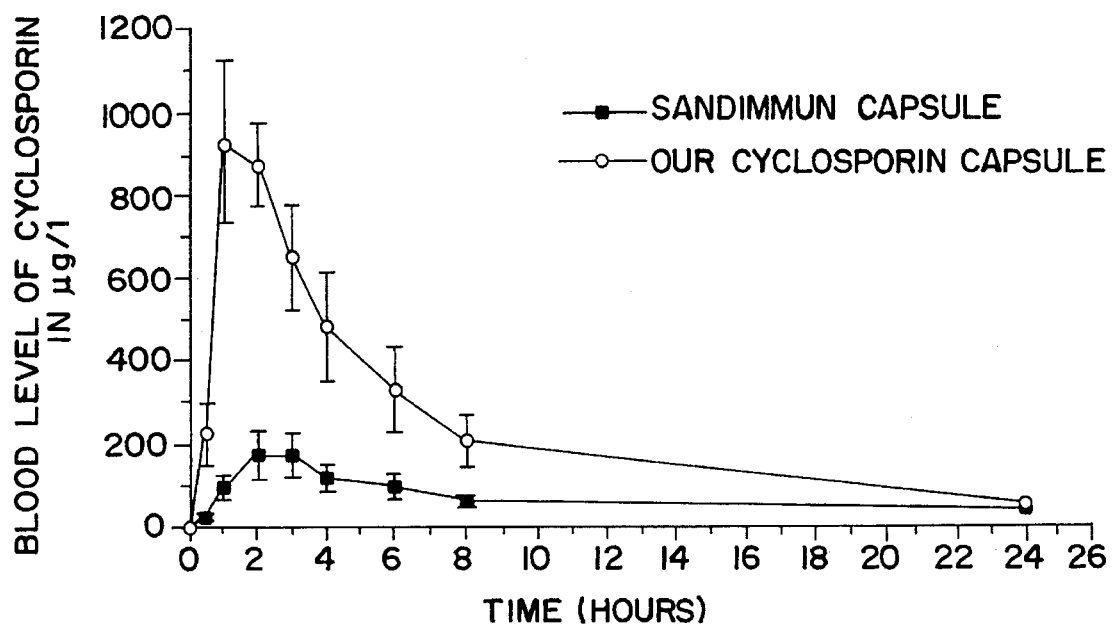
Figure 2:
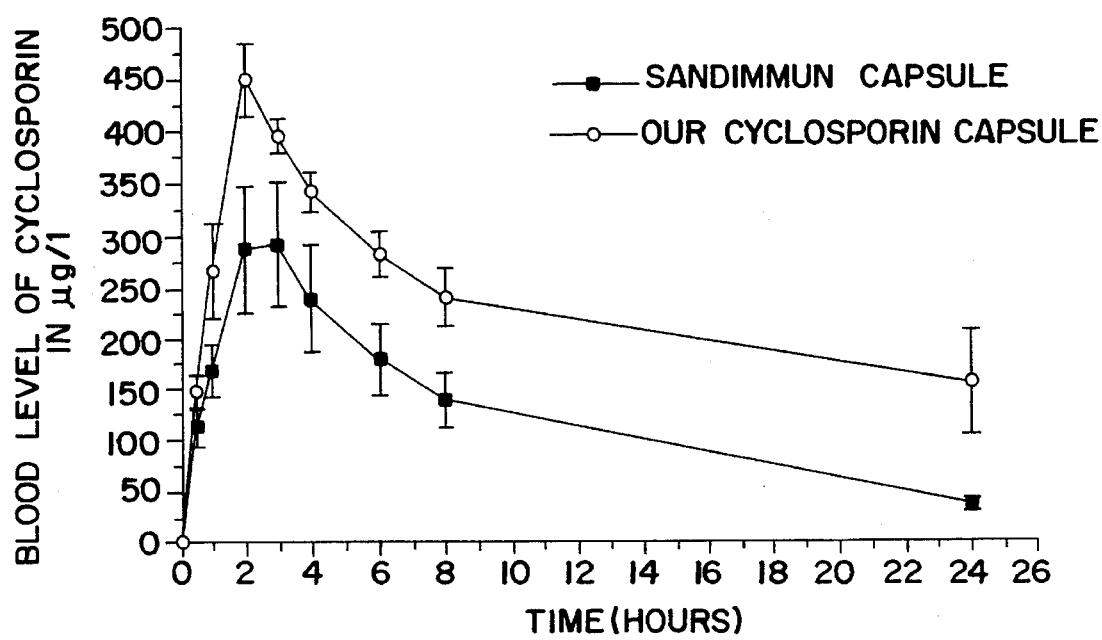

Conditions: columns: LiChrosorb RP-18; 5 μm, 200×4.6 mm. Eluent: acetonitrile:methanol:buffer=59:10:31. Buffer: 0.2 ml of 85% phosphoric acid dissolved in 500 ml of distilled water. Flow rate: 1 ml/min. Column temperature: 70° C. Detection: in UV range at 210 nm. The data obtained are presented in the following table.

Results of the stability test of the composition according to Example 3 and the active ingredient content in % by weight are presented in the table. (Starting content of active ingredient is: 10.4% by weight.)

|  | 1 month | 2 months | 3 months | 12 months |
|---|---|---|---|---|
| 60° C. | 9.90 | 10.00 | 10.10 | — |
| 50° C. | 10.00 | 10.10 | 10.10 | — |
| 40° C. | 10.10 | 10.20 | 10.20 | 10.10 |
| 25° C. | — | — | 10.20 | 10.12 |
| 25° C. | — | — | 10.20 | 10.20 |

On the basis of the results given above it can be assumed that the compositions according to the invention do not require special storage conditions. From the measured values it can be concluded, that the active ingredient content of the compositions stored in a cool place (5°–15° C.) is still sufficient even 4–5 years later, and it can be used for therapeutic purposes.

The present invention is illustrated by the following examples without limitation of the scope of the invention.

EXAMPLE 1

| Cyclosporin A | 100 g |
|---|---|
| Vitamin E TPGS | 300 g |
| Absolute ethanol | 100 g |
| Miglyol 812 | 500 g |
| TOTAL | 1000 g |

The Vitamin E TPGS is dissolved in the Miglyol 812 at 35°–40° C., absolute ethanol is added, then the cyclosporin A is dissolved at 35° C. in it. The solution is filtered through Sartorius SM 11604 regenerated cellulose membrane. The filtered solution is filled at 30° C. into oval soft gelatin capsule No. 5 or hard gelatin capsule No. 3, and the capsules are sealed. The filling weight is 250 mg, the active ingredient content is 25 mg.

EXAMPLE 2

| Cyclosporin A | 100 g |
|---|---|
| Vitamin E TPGS | 96 g |
| Absolute ethanol | 192 g |
| Sorbitan monolaurate | 192 g |
| Miglyol 812 | ad 1000 ml |

The Vitamin E TPGS is dissolved in the Miglyol 812 at 35°–40° C., absolute ethanol is added, then the cyclosporin A is dissolved at 35° C. in it, and the mixture is homogenized with the sorbitan monolaurate. The homogenous solution is filtered through Sartorius SM 11604 regenerated cellulose membrane, then filled into bottles suitable for dosing drink-solution and thoroughly capped. All phases of the technological process are carried out under aseptic conditions.

The solution of 0.96 g/cm$^3$ specific gravity contains 100 mg/ml of cyclosporin A.

EXAMPLE 3

| Cyclosporin A | 105 g |
|---|---|
| Vitamin E TPGS | 150 g |
| Absolute ethanol | 200 g |
| Sorbitan monololeate | 150 g |
| Miglyol 812 | 395 g |
| TOTAL | 1000 g |

The solution is prepared as described in Example 2. The solution is worked up as drink-solution according to Example 2, or filled into oval soft gelatin capsule No. 5. The solution of 0.95 g/cm$^3$ specific gravity contains 100 mg/ml of cyclosporin A, or in case of soft gelatin capsule 0.25 ml of filling contains 25 mg of cyclosporin A.

EXAMPLE 4

| Cyclosporin A | 150 g |
|---|---|
| Vitamin E TPGS | 150 g |
| 96 vol. % ethanol | 200 g |
| Sorbitan monostearate | 150 g |
| Isopropyl myristate | 350 g |
| TOTAL | 1000 g |

The Vitamin E TPGS and the sorbitan monostearate are dissolved in isopropyl myristate at 35°–40° C., then 96 vol. % ethanol is added, and the cyclosporin A is dissolved at 35° C. in it. The homogenous solution is filtered through Sartorius SM 11604 regenerated cellulose membrane, then filled into oval soft gelatin capsule No. 6. The filling weight of the capsule is 333 mg, and it contains 50 mg of cyclosporin.

EXAMPLE 5

| Cyclosporin A | 100 g |
|---|---|
| Vitamin E TPGS | 100 g |
| Absolute ethanol | 100 g |
| Sorbitan monooleate | 150 g |
| Miglyol 812 | 200 g |
| Citroflex-2 | 350 g |
| TOTAL | 1000 g |

The Vitamin E TPGS is dissolved in the Miglyol 812 at 35°–40° C., then it is mixed with absolute ethanol and Citroflex-2, and then the cyclosporin A is dissolved at 35° C. in it. The mixture is homogenized with the sorbitan monooleate. The homogenous solution is filtered through Sartorius SM 11604 regenerated cellulose membrane. The filtered solution is filled into oval soft gelatin capsule No. 5. One capsule contains 25 mg of cyclosporin.

EXAMPLE 6

| Cyclosporin G | 100 g |
|---|---|
| Vitamin E TPGS | 150 g |
| Absolute ethanol | 150 g |
| Sorbitan monopalmitate | 150 g |
| Citroflex-2A | 100 g |
| Sunflower oil | ad 1000 ml |

The Vitamin E TPGS and the sorbitan monopalmitate is dissolved in the sunflower oil at 35°–40° C. The solution is mixed with absolute ethanol, then the cyclosporin G is dissolved at 35° C. in it. The mixture is homogenized with the Citroflex-2A. The solution obtained is filtered through regenerated cellulose membrane with a pore size of 0.80 μm, then it is filled into soft gelatin capsule No. 10. One capsule contains 50 mg of cyclosporin G.

EXAMPLE 7

| Cyclosporin A | 300 g |
|---|---|
| Vitamin E TPGS | 150 g |
| Absolute ethanol | 200 g |
| Hostaphat KL 340 N | 100 g |
| Sesame oil | 250 g |
| TOTAL | 1000 g |

The Vitamin E TPGS is dissolved in the sesame oil at 35°–40° C. The solution is mixed with absolute ethanol, then the cyclosporin A is dissolved in the mixture and homogenized with the Hostaphat KL 340 N. The homogenous solution is filtered through regenerated cellulose membrane with a pore size of 0.80 μm, and filled into soft gelatin capsule No. 6. One capsule contains 100 mg of cyclosporin A.

EXAMPLE 8

| Cyclosporin G | 50 g |
|---|---|
| Vitamin E TPGS | 50 g |
| Absolute ethanol | 200 g |
| Sorbitan monolaurate | 100 g |
| Olive oil | 250 g |
| TOTAL | 1000 g |

The Vitamin E TPGS is dissolved in the olive oil at 35°–40° C. The solution is mixed with absolute ethanol, then the cyclosporin G is dissolved in the mixture and homogenized with the sorbitan monolaurate. The homogenous solution is filtered through regenerated cellulose membrane with a pore size of 0.45 μm, and filled into soft gelatin capsule No. 5. One capsule contains 12.5 mg of cyclosporin G.

EXAMPLE 9

The process described in Example 8 is followed, but instead of capsule the product is filled into bottles suitable for dosing drink-solution. All steps of the production are carried out under aseptic conditions.

EXAMPLE 10

| | |
|---|---|
| Cyclosporin A | 100 g |
| 60 vol. % of Vitamin E TPGS solution in polyethylene glycol 200 | 150 g |
| Absolute ethanol | 50 g |
| Sorbitan monooleate | 150 g |
| Citroflex-2 | 550 g |
| TOTAL | 1000 g |

The Vitamin E TPGS dissolved in polyethylene glycol is mixed with absolute ethanol and Citroflex-2. The cyclosporin A is dissolved in the mixture at 35° C., and homogenized with sorbitan monooleate. The solution obtained is filtered through Sartorius SM 11604 regenerated cellulose membrane, then filled into oval soft gelatin capsule No. 5. One capsule contains 25 mg of cyclosporin A.

We claim:

1. An oral multiple emulsion pre-concentrate composition, comprising cyclosporin, ethanol, a lipophilic solvent, tocopheryl polyethylene carboxylic acid ester as surfactant, and a co-tenside.

2. The composition according to claim 1, wherein the lipophilic solvent is a fatty acid glyceride ester.

3. The composition according to claim 1, wherein the co-tenside is a tenside of 4–10 HLB value.

4. The composition according to claim 1, wherein the co-tenside is a sorbitan fatty acid ester.

5. The composition according to claim 1, wherein the co-tenside is an alkyl polyglycolether orthophosphoric acid ester.

6. The composition according to claim 1, wherein the surfactant is d-α-tocopheryl polyethylene glycol 1000 succinate.

7. The composition according to claim 6, wherein the tocopheryl polyethylene glycol 1000 succinate is in the form of a polyethylene glycolic solution.

8. The composition according to claim 1, wherein cyclosporin is present in an amount of from about 5 to about 30% by weight;

ethanol is present in an amount of from about 5 to about 20% by weight;

the lipophilic solvent is present in an amount of from about 20 to about 55% by weight;

the tocopheryl polyethylene glycol carboxylic acid ester is present in an amount of from about 5 to about 30% by weight; and the co-tenside is present in an amount of from about 10 to about 20% by weight.

9. The composition according to claim 1, further comprising an amphiphilic solvent.

10. The composition according to claim 9, wherein the amphiphilic solvent is present in an amount of from about 10 to about 55% by weight.

11. An oral multiple emulsion pre-concentrate composition, comprising cyclosporin, ethanol, an amphiphilic solvent, tocopheryl polyethylene carboxylic acid ester as surfactant, and a co-tenside.

12. The composition according to claim 11, wherein the amphiphilic solvent is present in an amount of from about 10 to about 55% by weight.

13. The composition according to claim 11, wherein the amphiphilic solvent is a pharmaceutically acceptable alkyl ester of $C_{2-8}$ polycarboxylic acid.

14. The composition according to claim 13, wherein the alkyl ester of $C_{2-8}$ polycarboxylic acid is acetyl triethyl citrate.

* * * * *

UNITED STATES PATENT AND TRADEMARK OFFICE
CERTIFICATE OF CORRECTION

PATENT NO.: 5,583,105

DATED: December 10, 1996

INVENTOR(S): KOVÁCS et al.

It is certified that error appears in the above-identified patent and that said Letters Patent is hereby corrected as shown below:

On the cover page, item [30], "[DE]   Germany" should read --[HU]   Hungary--.

Signed and Sealed this

Twenty-fifth Day of February, 1997

Attest:

BRUCE LEHMAN

*Attesting Officer*  *Commissioner of Patents and Trademarks*